US00PP17279P2

(12) United States Plant Patent
Clifford et al.

(10) Patent No.: US PP17,279 P2
(45) Date of Patent: Dec. 12, 2006

(54) ***HOSTA* PLANT NAMED 'CLIFFORD'S STINGRAY'**

(50) Latin Name: *Hosta hybrida*
Varietal Denomination: Clifford's Stingray

(76) Inventors: John K. Clifford, Clifford's Perennial & Vine, Inc., P.O. Box 473, Paw Paw, MI (US) 49079; Ken J. Clifford, Clifford's Perennial & Vine, Inc., P.O. Box 473, Paw Paw, MI (US) 49079

( * ) Notice: Subject to any disclaimer, the term of this patent is extended or adjusted under 35 U.S.C. 154(b) by 10 days.

(21) Appl. No.: 11/224,435

(22) Filed: Sep. 12, 2005

(51) Int. Cl.
*A01H 5/00* (2006.01)

(52) U.S. Cl. ..... Plt./353

(58) Field of Classification Search ..... Plt./353
See application file for complete search history.

*Primary Examiner*—Wendy Haas
(74) *Attorney, Agent, or Firm*—Penny J. Aguirre

(57) ABSTRACT

A new cultivar of *Hosta* named 'Clifford's Stingray', a sport of *Hosta* 'Fire and Ice', that is characterized by its unique variegated foliage with narrow, white streaked centers, wide dark green margins and an intermediate streaked area of bright green. 'Clifford's Stingray' has an upright plant habit, a vigorous growth rate, and unique pale lavender flowers that are held in a congested whorl just above the foliage in mid to late summer.

1 Drawing Sheet

Botanical classification: *Hosta hybrida.*
Cultivar designation: 'Clifford's Stingray'.

BACKGROUND OF THE INVENTION

The present invention, *Hosta* 'Clifford's Stingray', relates to a new and distinct cultivar of *Hosta hybrida* and hereinafter referred to as 'Clifford's Stingray'.

The inventors discovered the new cultivar, 'Clifford's Stingray', in summer of 2002 a in a nursery in Paw Paw, Mich. 'Clifford's Stingray' was discovered as a naturally occurring whole plant mutation among containers of *Hosta* 'Fire and Ice' (not patented). 'Clifford's Stingray' is presumed to be a sport of 'Fire and Ice' as the containers had been planted with plugs produced by tissue culture of 'Fire and Ice'.

Asexual reproduction of the new cultivar was first accomplished under the direction of the inventors utilizing *in vitro* propagation in a tissue culture lab in Florida in 2002. Asexual reproduction of the new cultivar by division and tissue culture has shown that the unique features of 'Clifford's Stingray' are stable and reproduced true to type in successive generations.

SUMMARY OF THE INVENTION

The following traits have been repeatedly observed in trials in Michigan for a period of two years and represent the characteristics of the new cultivar. These attributes in combination distinguish 'Clifford's Stingray' as a new and unique cultivar of *Hosta.*

1. The foliage of 'Clifford's Stingray' is variegated with narrow white centers, wide dark green margins and bright green areas or streaks that are present between the centers and margins (intermediate areas). The margins comprise from one half to three fourths on the leaf area. The variegation pattern of 'Clifford's Stingray' differs from the parent plant, 'Fire and Ice', in the following characteristics: the center areas of 'Clifford's Stingray' are much narrower and more streaked, the margins are much wider, and there is a greater amount of intermediate coloration.
2. 'Clifford's Stingray' has a heavy substance with thicker leaves than 'Fire and Ice'.
3. 'Clifford's Stingray' is a vigorous grower in comparison to 'Fire and Ice'.
4. 'Clifford's Stingray' blooms in mid to late summer with pale lavender flowers that open just above the foliage. The flowers are arranged on very short pedicels and very short internodes resulting in a unique congested whorl of flowers at the top of the flower scapes.

BRIEF DESCRIPTION OF THE DRAWING

The accompanying colored photograph illustrates the overall appearance and distinct characteristics of the new *Hosta.* The photograph was taken in July of a two year-old plant of 'Clifford's Stingray' as grown outdoors in a trial garden in New Hope, Minn. The colors in the photographs are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of two year-old plants of the new cultivar as grown outdoors in Michigan and Minnesota. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Clifford's Stingray' is a cultivar of *Hosta hybrida.*

Parentage: Naturally occurring sport of *Hosta* 'Fire and Ice'.

General description:

*Blooming period.*—About 3 weeks from mid July to mid August in Michigan.

*Plant habit.*—Herbaceous perennial, clump-forming, upright habit of medium sized leaves.

*Height and spread.*—Reaches about 20 to 25 cm in height and up to about 30 cm in width.

*Hardiness.*—U.S.D.A Zones 3 to 8.

*Culture.*—Light to full shade, moist soils of moderate fertility.

*Diseases and pests.*—Heavy substance should confers resistance to slugs. No susceptibility or resistance to diseases or other pests has been observed for 'Clifford's Stingray'.

*Root description.*—Freely branched, fleshy.

*Propagation.*—*In vitro* propagation is the preferred method utilizing typical methods for *Hosta,* division are also possible.

*Growth rate.*—Vigorous.

Foliage description:

*Leaf shape.*—Ovate.

*Leaf division.*—Simple.

*Leaf base.*—Cordate.

*Leaf apex.*—Acuminate.

*Leaf venation.*—About 11 pairs of veins, camptodrome pattern, impressed on upper surface and raised on lower surface, color matches leaf coloration.

*Leaf margins.*—Entire, a few slight indentations.

*Leaf attachment.*—Petiolate.

*Leaf arrangement.*—Basal, radiate spirally from base.

*Leaf surface.*—Glabrous on upper surface and glaucous on lower surface.

*Leaf substance.*—Heavy.

*Leaf orientation.*—Held upright to a 15° angle to petiole axis.

*Leaf color.*—Emerging foliage, upper surface; centers 5D and 2D toward leaf base, margins 137A, intermediate area between the margins and centers 144B, lower surface; centers 2D, margins 189A, intermediate area 145A. Mature foliage, upper surface; centers 4D, margins a color between 137A and 147A (very dark), intermediate area 144A (slightly darker) and areas of 191A, lower surface; centers 4D, margins 137A with glaucous coat of N138C, intermediate area 137D and a few areas of 191A.

*Leaf variegation pattern.*—Dark green margins comprise about one half to three quarters of the leaf area, white center pattern is narrow and most often streaked, intermediate area between margin and centers is streaks of bright green and occasional grey-green areas.

*Leaf size.*—Average of 16 cm in length, about 11 cm in width when mature.

*Leaf quantity.*—About 5 to 7 per shoot (eye).

*Petiole size.*—About 12 cm in length, about 1.4 cm in width.

*Petiole aspect.*—Held upright or up to a 45° angle from vertical.

*Petiole color.*—Inner surface 2D with margins 137A and a few thin stripes of 144A, outer surface 4D with thin margin of 137A.

*Petiole surface.*—Glabrous.

*Petiole shape.*—Sulcate.

Flower scape description:

*Scape shape.*—Round, solid, robust.

*Scape number.*—One per mature eye under normal growing conditions.

*Scape posture.*—Straight, held upright.

*Scape size.*—About 35 cm in length to base of flower cluster, about 7 mm in width.

*Scape color.*—158B.

*Scape surface.*—Glabrous.

*Leaf bracts.*—Average of 3 per scape, centers are 158B in color, margins are 144A in color, ovate in shape, average of 2 cm in length and 1 cm in width, all occur with 2 cm of flower cluster.

Flower description:

*Inflorescence type.*—Terminal racemes of single tubular-shaped flowers, flowers are tightly packed near terminus of scape in a whorl, branching frequently occurs at the terminus to create a palm tree like form at maturity.

*Lastingness of inflorescence.*—About 2 to 3 weeks from first opening bloom to fading of last opening bloom.

*Flower shape.*—Tubular-shaped.

*Flower number.*—About 25 to 30.

*Flower internode length.*—Flowers are in a cluster at terminus and not elongated on scape.

*Flower fragrance.*—None detected.

*Flower bud shape.*—Spathulate.

*Flower bud size.*—Up to about 3.5 cm in length and 1 cm in diameter.

*Flower bud color.*—85D with tepal margins of N88C prior to opening.

*Flower size.*—About 5 cm in length and about 2 cm in diameter, tube portion is 1.5 cm and more expanded region is 3.5 cm.

*Flower color.*—N155B (slightly lighter) with markings of 85A (margins and shadings), overall color effect is very pale lavender.

*Pedicels.*—Very short, about 3 mm in length, 2 mm in diameter, N155B in color.

*Perianth features.*—Comprised of 6 tepals, 3 interior and 3 exterior, fused in tube region and one half of expanded region.

*Tepal shape.*—Oblanceolate.

*Tepal size.*—About 4.5 cm in length, about 8 mm in width.

*Tepal color.*—Outer and inner surfaces 155B (whiter than), thin margins and area near base of 85A, lower surface also has shadings of 85B and 85C in center of upper portion of tepal.

*Tepal texture.*—Glabrous.

*Floral bracts.*—1 per flower, ovate in shape, glabrous surface, centers are 158B in color, margins are 144A in color, up to 1.5 cm in length and 7 mm in width.

Reproductive organs:

*Gynoecium.*—1 Pistil. Style is about 4.5 cm in length (extends about 5 mm beyond perianth), 1 mm in width and 8D in color, stigma is 3-lobed and 155B in color. Ovary is superior, compound, oblong in shape, composed of 3 locules, 5 mm in length, 3 mm in width, 158B in color.

*Androecium.*—6 stamens. Filament is 155B in color, 4 cm in length, 1 mm in width, about the same length as perianth. Anthers are 3 mm in length, 2 mm in width, attachment is versatile, 202A in color, dehiscence is longitudinal. Pollen is abundant and 15C in color.

*Fruit.*—'Clifford's Stingray' has been observed to be sterile, no seed pods have been observed.

We claim:

1. A new and distinct cultivar of *Hosta* plant named 'Clifford's Stingray', as herein illustrated and described.

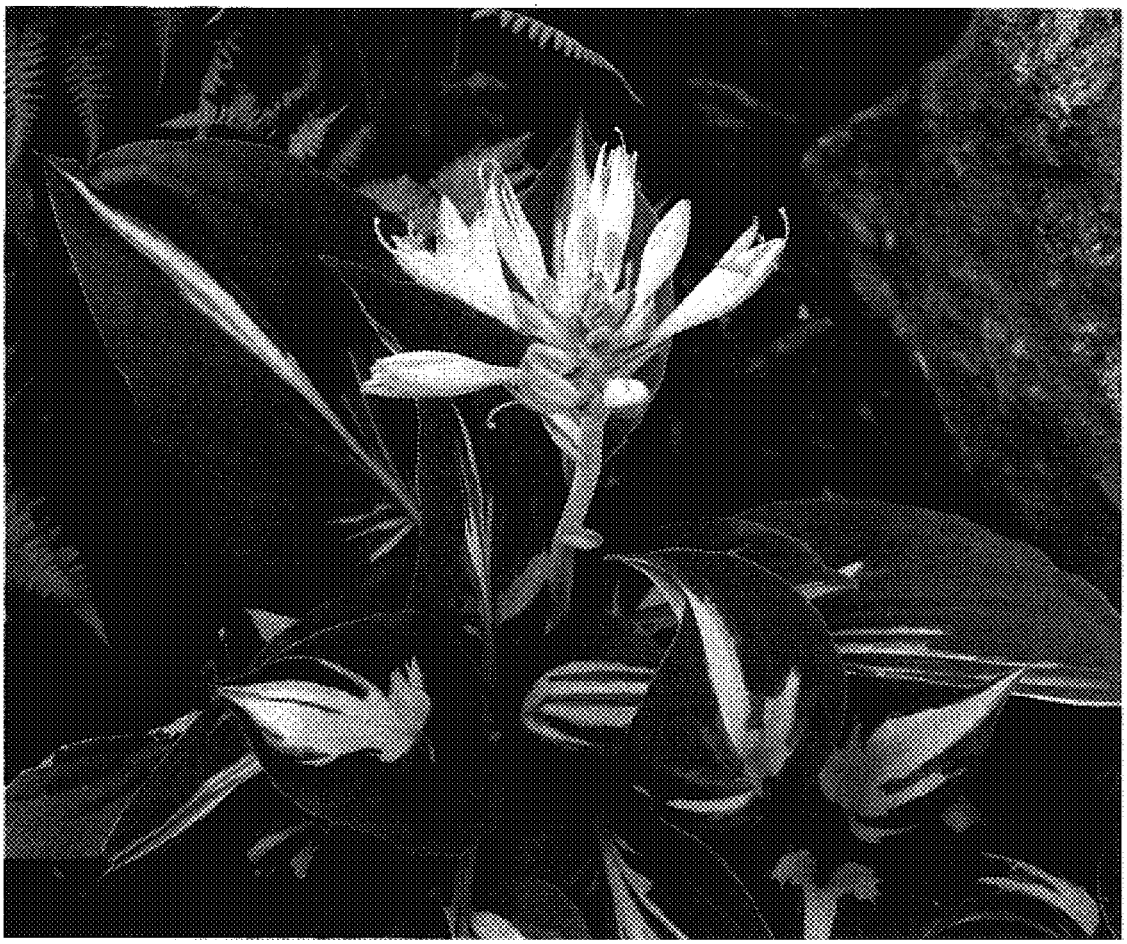

* * * * *